United States Patent
Suzuki et al.

(10) Patent No.: US 10,234,416 B2
(45) Date of Patent: Mar. 19, 2019

(54) ANION SENSOR (71) Applicant: HITACHI HIGH-TECHNOLOGIES CORPORATION, Tokyo (JP)

(72) Inventors: Akiko Suzuki, Tokyo (JP); Tetsuyoshi Ono, Tokyo (JP); Atsushi Kishioka, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/896,091

(22) PCT Filed: Apr. 21, 2014

(86) PCT No.: PCT/JP2014/061119
§ 371 (c)(1),
(2) Date: Dec. 4, 2015

(87) PCT Pub. No.: WO2015/008517
PCT Pub. Date: Jan. 22, 2015

(65) Prior Publication Data
US 2016/0131611 A1 May 12, 2016

(30) Foreign Application Priority Data
Jul. 19, 2013 (JP) .................................. 2013-150050

(51) Int. Cl.
*G01N 27/333* (2006.01)
*G01N 33/487* (2006.01)

(52) U.S. Cl.
CPC ..... *G01N 27/333* (2013.01); *G01N 33/48707* (2013.01)

(58) Field of Classification Search
CPC ...... G01N 27/30; G01N 27/302; G01N 27/31; G01N 27/36; G01N 27/333–27/401;
(Continued)

(56) References Cited

U.S. PATENT DOCUMENTS 4,686,012 A * 8/1987 Engell .................... C04B 35/16
204/419
5,045,171 A * 9/1991 MacDonald .......... C08J 5/2275
204/252

(Continued)

FOREIGN PATENT DOCUMENTS

| JP | 9-15190 A | 1/1997 |
| JP | 9-43191 A | 2/1997 |

(Continued)

OTHER PUBLICATIONS

K.P. Xiao, A Chloride Ion-Selective Solvent Polymeric Membrane Electrode Based on a Hydrogen Bond Forming Ionophore, Anal. Chem., vol. 69, pp. 1038-1044 (1997).*

(Continued)

*Primary Examiner* — Maris R Kessel
(74) *Attorney, Agent, or Firm* — Mattingly & Malur, PC (57) ABSTRACT

The present invention announces a method for extending the storage life of a test reagent for quantification of ionic components in samples by using an anion sensor. The purpose of the present invention is to provide an anion sensor, wherein the storage life of the anion sensor itself may be extended, to thereby extend the storage life of the anion sensor beyond that of conventional anion sensors. According to the present invention, through adjustment of the pH of the internal solution (internal gel liquid), it is possible to provide an anion sensor that maintains consistent performance, and has longer storage life.

2 Claims, 6 Drawing Sheets

(58) Field of Classification Search
CPC ............... G01N 27/403; G01N 27/414; G01N 33/48707; G01N 33/4875; G01N 35/085
See application file for complete search history.

(56) References Cited

U.S. PATENT DOCUMENTS 5,174,872 A * 12/1992 Scott ..................... G01N 33/84
204/416
2013/0121779 A1* 5/2013 Geiser ................... B23F 19/10
409/8

FOREIGN PATENT DOCUMENTS

| | | |
|---|---|---|
| JP | 9-61396 A | 3/1997 |
| JP | 10-307120 A | 11/1998 |
| JP | 10-318973 A | 12/1998 |
| JP | 2000-028568 A | 1/2000 |
| JP | 2000-329728 A | 11/2000 |
| JP | 3321461 B | 9/2002 |
| JP | 2003-207476 A | 7/2003 |
| JP | 4252383 B | 4/2009 |

OTHER PUBLICATIONS

International Search Report of PCT/JP2014/061119.
Extended European Search Report received in corresponding European Application No. 14826530.9 dated Mar. 1, 2017.

* cited by examiner

ANION SENSOR

TECHNICAL FIELD

The present invention relates to an anion sensor of an electrolyte analyzer, and an analyzer using the anion sensor.

BACKGROUND ART

An electrolyte analyzer is applied to determine the quantity of a specific ion component such as sodium ions, potassium ions, and chlorine ions, which are contained in a biological sample (referred to as a sample below) such as blood and urine. The concentration of specific ions in a biological fluid has a close relationship with a metabolic reaction of a living body. Various diagnoses such as hypertension symptoms, kidney diseases, and nerve disorders can be performed by measuring the concentration of specific ions.

As one of methods used in detection of ions in a sample, a method of measuring the amount of a specific ion in a sample by using an ion sensor has been known. In such a measurement using an ion sensor, first, a standard sample of a known concentration is measured in advance, and a calibration curve is calculated from a measurement result. A potential difference between an internal standard fluid and the sample is measured and the concentration of the specific ion in the sample is measured by using the potential difference and the calibration curve. In the ion sensor, the Nernst's expression (Expression 1) is established between an activity a of an ion which is a target and a potential E indicated by the ion sensor.

$$E=E0+2.303[RT/(ZF)] \log(a) \quad \text{Expression 1}$$

In Expression 1, R indicates a gas constant, and T indicates an absolute temperature. Z indicates a valency, and F indicates the Faraday constant. E0 indicates a standard electrode potential. If such an ion sensor is used, measurement of a potential enables determination of the quantity of the ion concentration.

As an anion sensor used in measurement of the chlorine ions, a solid membrane electrode using Ag/AgCl, a polymeric support liquid membrane electrode, or the like is used. The polymeric support liquid membrane electrode is obtained by holding a sensitive substance (ligand) in a polymeric support membrane formed of polyvinyl chloride and the like. The sensitive substance is formed from an organic compound. However, the latter sensor is generally used in the measurement of the chlorine ion in a biological fluid.

In the anion sensor, an anion exchange membrane is used. The anion exchange membrane uses an anion exchange resin film which contains a quaternary ammonium salt as an anion exchange group using a polymer as a basic skeleton. Selectivity for an anion in the quaternary ammonium salt depends on resolvability of an ion between the ion exchange membrane and a sample solution. A sequence of the selectivity uses a so-called Hofmeister series which relates to the hydration ability of ions, as a standard. For example, there is a problem in that if anions having high lipophilicity are present together, obtaining a measurement value of the chlorine ion is easily obstructed. Conventionally, many methods for improving anion selectivity have been proposed.

For example, PTL 1 discloses a method of performing coating treatment on a surface of the ion exchange membrane, which does not come into contact with the sample, with a two-liquid mixture-based epoxy resin, in order to prevent degradation of performance of a chlorine ion sensor.

PTL 2 discloses a method of performing manufacturing by using a manufacturing method in order to improve performance of a chlorine ion-sensitive membrane. The manufacturing method has a first process and a second process. In the first process, an anion exchange resin film is immersed into a solution obtained by dissolving meta-phenylenediamine in a solvent. In the second process, the anion exchange resin film impregnated with meta-phenylenediamine is immersed in a liquid mixture of formaldehyde and hydrochloric acid so as to generate a condensate of meta-phenylenediamine and formaldehyde.

PTL 3 discloses a method for improving preservability of a solution for an ion-selective electrode by containing an aminoglycoside antibiotic material in order to improve storing performance for consumable supplies in an ion sensor system.

PTL 4 discloses a diluted solution for an electrolyte analyzer, in which proliferation of bacteria is suppressed by adjusting a salt concentration and thus an antimicrobial effect is shown in the long term.

CITATION LIST

Patent Literature

PTL 1: JP-A-2003-207476
PTL 2: JP-A-10-318973
PTL 3: Japanese Patent No. 3321461
PTL 4: Japanese Patent No. 4252383

SUMMARY OF INVENTION

Technical Problem

PTL 1 and PTL 2 disclose a method for improving the performance of the anion sensor. However, no examination for storing properties thereof was performed. There is a problem in that if a period of time elapses from when the anion sensor is manufactured, performance of the anion sensor is deteriorated and thus accurate measurement is impossible.

The mechanism is not reported and a manufacturing method for extending a shelf life is not reported.

PTL 3 and PTL 4 disclose a method for preventing breeding of saprophyte in storing of the solution for an ion-selective electrode or the diluted solution as consumable supplies used in the ion sensor. However, no examination for the shelf life of the ion sensor itself was performed.

Considering the problems, the present invention is to provide an anion sensor having a shelf life longer than that of the conventional anion sensor by extending the shelf life of the ion sensor itself.

Solution to Problem

The present invention is realized by adjusting the pH of an internal solution (internal gel liquid) in the anion sensor.

Advantageous Effects of Invention

According to the present invention, an anion sensor which maintains stable performance and has a longer shelf life can be provided.

DESCRIPTION OF EMBODIMENTS

Hereinafter, the present invention will be described in detail with reference to the drawings by using an example. First, an example of an anion sensor using an anion exchanger according to the present invention will be described.

The ion sensor in the present invention is included in an automatic clinical chemical analyzer as illustrated in FIG. 7 and is used in many cases. For example, in a device configuration of FIG. 7, a reagent is dispensed from a pump 107 for a sample to a dilution tank 130. A sample is aspirated from a sample container 101 by using an aspiration pump 126. The sample container 101 is held on a sample disk by a sampling probe 127. The measurement sample is caused to flow into an ion sensor 128. A generated potential is subjected to signal processing through an AD converter 129.

In the ion sensor, ion sensors which can measure plural types of ions may be disposed in parallel, but at least an anion sensor is included. The anion sensor is configured by a polymeric support liquid membrane electrode. The polymeric support liquid membrane electrode is obtained by holding a sensitive substance (ligand) in a polymeric support membrane formed of polyvinyl chloride and the like. The sensitive substance is formed from an organic compound. As the anion sensor, an anion exchange resin material is used. The anion exchange resin material contains a quaternary ammonium salt as an anion exchange group by using a polymer as a basic skeleton and is subjected to coating treatment.

Example 1

Figure 1:
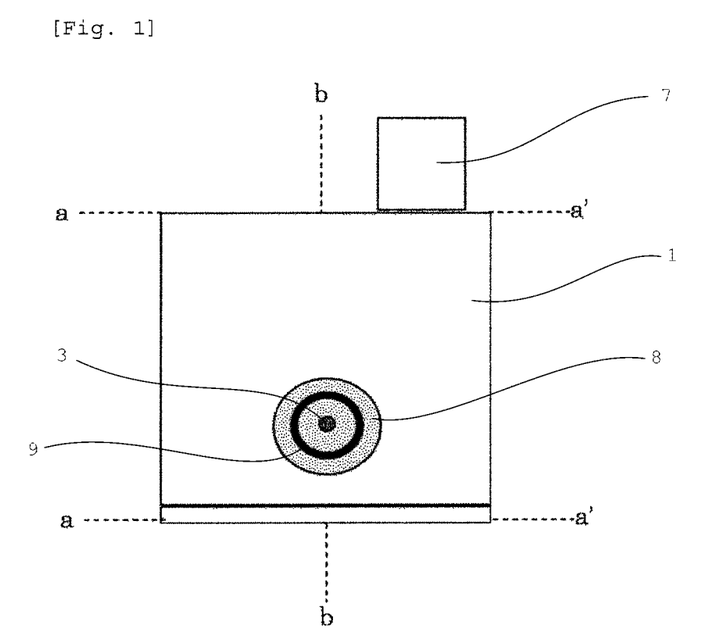
FIG. 1 is a center view of a flow cell type anion sensor.
Figure 2:
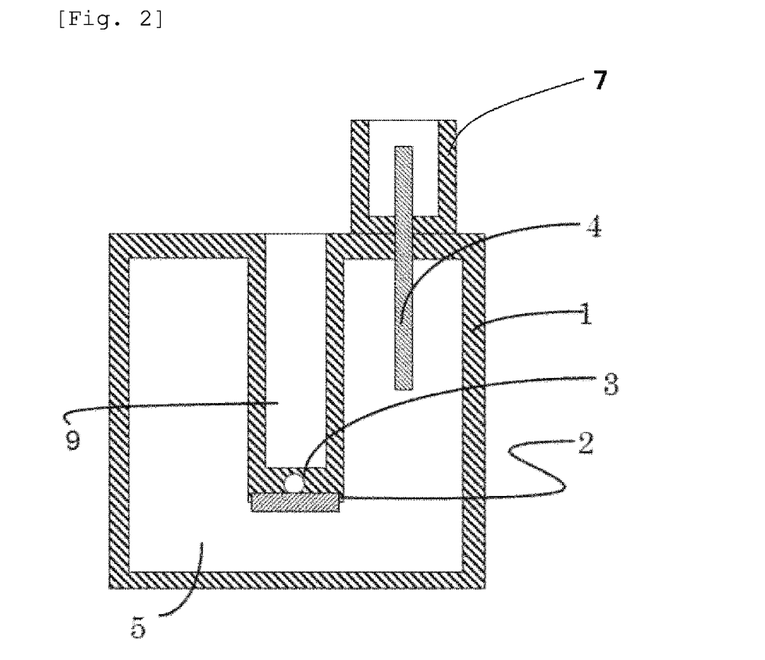
FIG. 2 is a cross-sectional view of the flow cell type anion sensor (cross-sectional view of a surface having an upper end a-a' and a lower end a-a' in FIG. 1).

FIG. 1 is a center view illustrating a configuration of a flow cell type anion sensor in Example 1 of the present invention. FIG. 2 is a cross-sectional view of a surface obtained by linking an upper end a-a' and a lower end a-a' in FIG. 1. The configuration of the ion sensor is not limited to the flow type. A configuration in which an anion exchanger of the ion sensor comes into contact with the sample may be made.

A flow channel 3, a chlorine ion-sensitive membrane 2, an internal electrode 4, and a space 5 are disposed in a rectangular parallelepiped flow cell type sensor body 1. A liquid of a measurement target passes through the flow channel 3 and a hole is provided in a portion of the flow channel 3. The chlorine ion-sensitive membrane 2 is disposed around the hole so as to come into contact with the liquid flowing in the flow channel via the hole of the flow channel. The internal electrode 4 outputs a potential occurring in the chlorine ion-sensitive membrane 2. The space 5 is used for accommodating an internal solution (internal gel liquid) which electrically connects the internal electrode 4 and the chlorine ion-sensitive membrane. The chlorine ion-sensitive membrane 2 is an anion exchanger which is subjected to coating treatment with an amine compound and has a quaternary ammonium salt. As long as an object shows a function as an anion sensor, the anion sensor is not limited to the chlorine ion-sensitive membrane. The flow channel 3 is formed so as to cross the sensor body 1 in a direction vertical to the surface of the paper on which FIGS. 1 and 2 are illustrated. The diameter of the flow channel 3 is about 1 mm. The internal electrode 4 formed from Ag/AgCl is provided in the flow cell sensor body 1. The internal electrode 4 is electrically connected to the chlorine ion-sensitive membrane 2 through the internal solution (internal gel liquid) in the space 5. It is possible to measure the concentration of chlorine ions contained in the liquid which flows in the flow channel 3, by measuring the potential of the internal electrode.

A concave portion 9 is formed in the center portion of FIG. 2. When the anion sensor is provided in the automatic clinical chemical analyzer, setting of the sensor at a predetermined position is enabled by gripping the concave portion 9.

Figure 3:
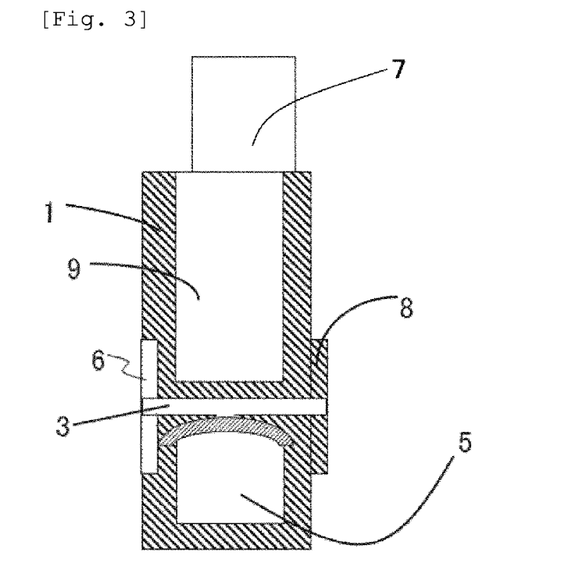
FIG. 3 is a cross-sectional view of the flow cell type anion sensor (cross-sectional view of an upper end b and a lower end b in FIG. 1).
Figure 4:
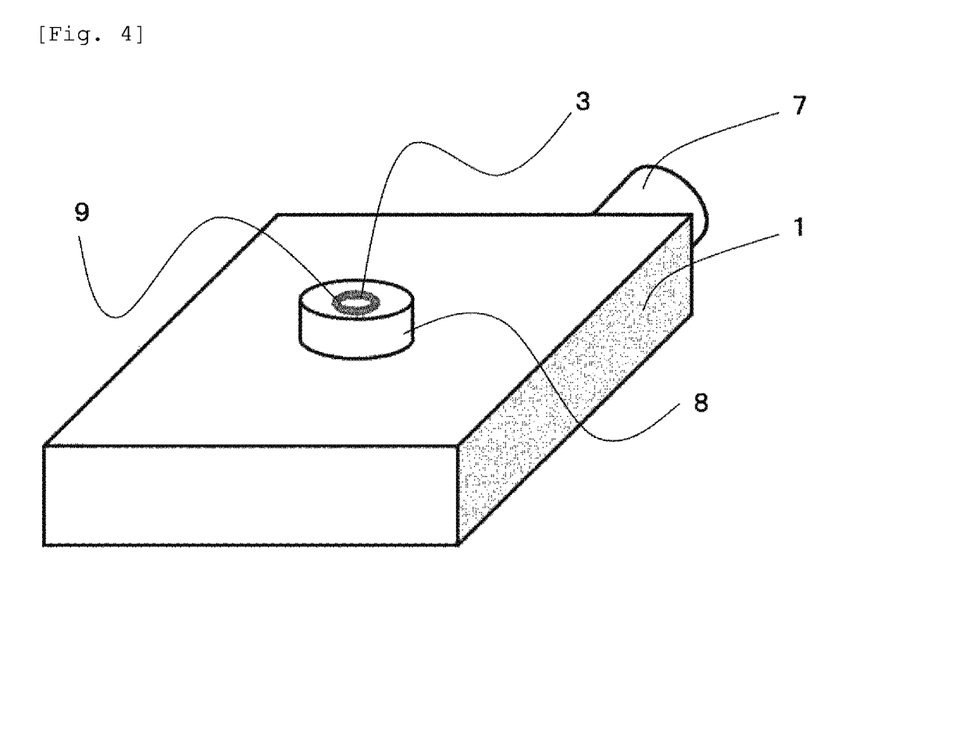
FIG. 4 is a perspective view of the flow cell type anion sensor.

FIG. 3 is a cross-sectional view of an upper end b and a lower end b of the anion sensor in FIG. 1. FIG. 4 is a perspective view of the anion sensor.

As is apparent from FIG. 3, the chlorine ion-sensitive membrane 2 is disposed on the flow channel side so as to have a convex shape. One side of the chlorine ion-sensitive membrane 2 comes into contact with the liquid flowing in the flow channel through the hole of the flow channel 3. Another side of the chlorine ion-sensitive membrane 2 comes into contact with the internal solution (internal gel liquid) which fills the space 5.

When a plurality of flow cell type sensors is arranged and used, in order to bond the sensors, it is desired that a convex portion 8 and a concave portion 6 are provided. The columnar convex portion 8 is provided on one side of a surface in which the flow channel 3 having a diameter of 1 mm is formed. The concave portion 6 engages with the convex portion 8 on the opposite side of the surface. When the plurality of flow cell type sensors is arranged and used, the convex portion 8 of the flow cell type sensor is put into the concave portion 6 of another adjacent flow cell type sensor, and thus the flow channel 3 performs communication without shifting. In this case, the flow cell type sensors detect different types of ions and may continuously measure ion concentrations of the plural types of ions by sequentially introducing the sample liquid into the flow channel.

FIG. 4 is a perspective view when the anion sensor is placed so as to cause the convex portion 8 to be directed upward. The flow channel 3 having a diameter of 1 mm is formed in the convex portion 8. An O-ring 9 for liquid leakage prevention is provided so as to surround the flow channel 3.

An evaluation method of the measuring method for the chlorine ion by using the anion sensor is as follows. In the evaluation of anion selectivity, considering an influence of $HCO_3$ ions having the strongest influence in blood serum among interfering ions to the chlorine ion-sensitive membrane, an $HCO_3$ selection coefficient was set as an evaluation target. The $HCO_3$ selection coefficient was evaluated by using the same method as that in PTL 2. The outline is as follows. $HCO_3$ ions are added as the interfering ions to the sample solution containing chlorine ions, and the $HCO_3$ selection coefficient is obtained by using the Nicolsky-Eisenmann expression. As an index of the performance of the anion sensor, the anion selectivity becomes excellent as the value of the $HCO_3$ selection coefficient becomes smaller. Determination of deterioration of the performance in storing was performed at a time when the $HCO_3$ selection coefficient reached 0.3.

The internal solution (internal gel liquid) was prepared as follows.

A buffer solution for stabilizing pH more was used in the internal solution (internal gel liquid), but it is not limited to any particular buffer solution. Since management of pH was difficult if the buffer solution had pH equal to or greater than 11, the pH buffer solution using NaCl and KCl as a base was added. There is no problem in a case where pH becomes pH 3.7, pH 4.9, pH 7.6, pH 9.0, pH 10.0, and pH 11.0 and the concentration of the chlorine ions in the internal solution (internal gel liquid) is equal to or greater than 1 mmol/L. However, here, the internal solution was prepared so as to have a concentration of 90 mmol/L to 100 mmol/L. The pH buffer solution uses a good buffer solution or a clinical chemical buffer solution, for example.

Specific examples of the good buffer solution include an MES(2-(N-Morphilino)ethanesulfonic acid) buffer solution, a Bis-Tris(Bis(2-hydroxyethyl)iminotris(hydroxymethyl) methane) buffer solution, an ADA(N-(2-Acetamido)iminodiacetic acid) buffer solution, a PIPES(Piperazine-N,N'-bis(2-ethanesulfonic acid) buffer solution, an ACES(N-(2-Acetamido)-2-aminoethanesulfonic acid) buffer solution, a MOPSO(3-(N-Morpholino)-2-hydroxypropanesulfonic acid) buffer solution, a BES(N,N-Bis(2-hydroxyethyl)-2-aminoethanesulfonic acid) buffer solution, a MOPS(3-(N-Morpholino)propanesulfonic acid) buffer solution, a TES(N-Tris(hydroxymethyl)methyl-2-aminoethanesulfonic acid) buffer solution, an HEPES(N-2-hydroxyethylpiperazine-N'-2-ethanesulfonic acid) buffer solution, a DIPSO(3-[N,N-Bis(2-hydroxyethyl)amino]-2-hydroxypropanesulfonic acid) buffer solution, a TAPSO(N-Tris(hydroxymethyl)methyl-2-hydroxy-3-aminopropanesulfonic acid) buffer solution, a POPSO(Piperazine-N,N'-bis(2-hydroxypropanesulfonic acid) buffer solution, an HEPPSO(N-2-Hydroxyethylpiperazine-N-2-hydroxypropane-3-sulfonic acid) buffer solution, an EPPS(N-2-Hydroxyethylpiperazine-N'-3-propanesulfonic acid, nick name: HEPPS) buffer solution, a Tricine (Tris(hydroxymethyl)methylglycine) buffer solution, a Bicine(N,N-Bis(2-hydroxyethyl)glycine) buffer solution, a TAPS(N-Tris(hydroxymethyl)methyl-3-aminopropanesulfonic acid) buffer solution, a CHES(2-(Cyclohexylamino)ethanesulfonic acid) buffer solution, a CAPSO(3-N-Cyclohexylamino-2-hydroxypropanesulfonic acid) buffer solution, a CAPS (3-Cyclohexylaminopropanesulfonic acid) buffer solution, and the like.

Specific examples of the clinical chemical buffer solution include an ammonium chloride buffer solution, a sodium acetate buffer solution, citric acid-the second sodium phosphate, hydrochloric acid-veronal sodium-sodium acetate, the first potassium phosphate-the second sodium phosphate, the first potassium phosphoric acid-borax, the first potassium phosphoric acid-sodium hydroxide, hydrochloric acid-collidine, hydrochloric acid-sodium veronal, hydrochloric acid-trisaminomethane, hydrochloric acid-borax, boric acid-sodium carbonate, boric acid-borax, hydrochloric acid-amino methyl propane diol, ammonium chloride-ammonia, glycine-sodium hydroxide, boric acid-sodium hydroxide, hydrochloric acid-dimethyl glycine sodium, borax-sodium hydroxide, borax-sodium carbonate, a Sorensen buffer solution, glycine-sodium chloride-hydrochloric acid, the second sodium citrate-hydrochloric acid, the second sodium citrate-sodium hydroxide, borax-sodium chloride, a Michaelis buffer solution, veronal sodium-sodium acetate-hydrochloric acid, a Clark-Rubus buffer solution, boric acid-potassium chloride-sodium hydroxide, an Atkins-Panchin buffer solution, a Paris tissue buffer solution, a Korutohofu buffer solution, an Mac-yl Bain buffer solution, a Hasuchingu-Sendoroi buffer solution, a Britton-Robinson buffer solution, a maleate buffer solution, a tris-maleate buffer solution, a veronal buffer solution, a veronal-acetate buffer solution, and the like. The clinical chemical buffer solution is not limited to these solutions.

In this example, when the internal solution having pH 3.7 and pH 4.9 was adjusted, the sodium acetate buffer solution was used. When the internal solution (internal gel liquid) having pH 7.6 and pH 9.6 was adjusted, the CHES buffer solution was used. When the internal solution (internal gel liquid) having pH 11.0 was adjusted, the ammonium chloride buffer solution was used for easily adjusting pH and the concentration of Na ions, K ions, and Cl ions.

In this example, the ion exchanger which was similar to the ion exchanger disclosed in PTL 2 was used. However, the manufacturing method or composition is not limited to that. If an ion exchanger including a weakly basic functional group is used and coating treatment is performed with an amine compound, the present invention is effective.

Figure 5:
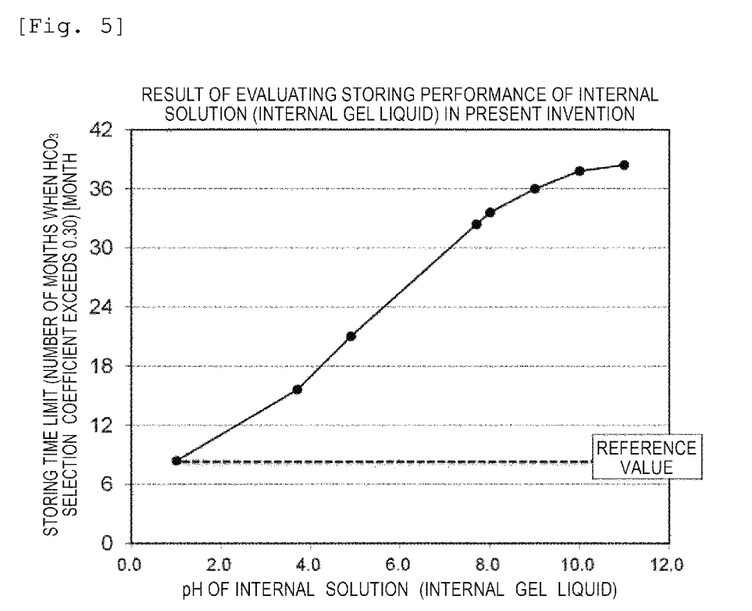
FIG. 5 illustrates a result of evaluating storing performance of an internal solution (internal gel liquid) in the present invention.
Figure 6:
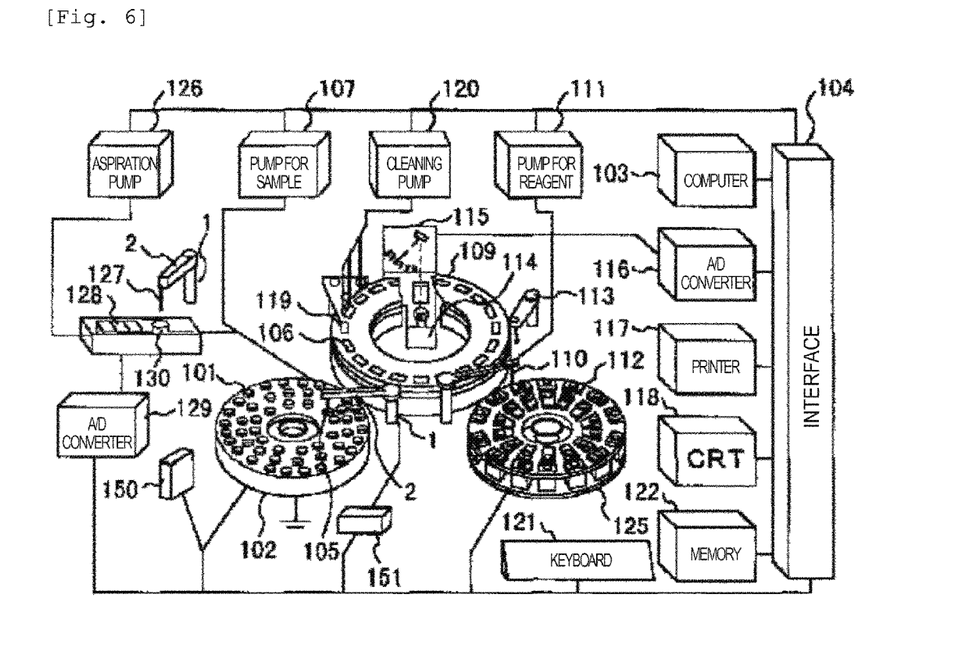
FIG. 6 is a configuration diagram of an automatic clinical chemical analyzer to which the present invention is applied.

FIG. 5 is a diagram illustrating a result of storing performance evaluation of the internal solution (internal gel liquid) in the present invention. As described above, the internal solution (internal gel liquid) having an adjusted pH value was manufactured and the anion sensor was filled with the internal solution. The $HCO_3$ selection coefficients in the internal solutions (internal gel liquid) having different pH values were measured and the shelf life of the anion sensor for each of pH values was examined. The $HCO_3$ selection coefficient was obtained and the anion selectivity was evaluated based on the shelf life of the anion sensor by using the above-described method. A transverse axis indicates the pH of the internal solution (internal gel liquid) and a longitudinal axis indicates shelf life (period of time expected that the $HCO_3$ selection coefficient exceeds 0.30). When the pH of the internal solution (internal gel liquid) is 3.7, the shelf life of the anion sensor has a value of twice a reference value. When the pH of the internal solution is 4.9, the shelf life of the anion sensor has a value of three times a reference value. When the pH of the internal solution is equal to or greater than 7.6, the internal gel liquid is not deteriorated even though storing is performed for two years or more. When the pH of the internal solution is from 9.0 to 11.0, the period of time is three years.

FIG. 5 corresponds to a graph obtained by plotting a measured value which is obtained and a measured value in a comparative example which will be described below. It is found that it is possible to significantly extend the shelf life by preparing the internal solution (internal gel liquid) so as to have a pH value in a range from acidity to alkalinity. If the pH value is set to be equal to or greater than 9.0, even though the anion sensor is disposed for a storing period of time of equal to or longer than three years, the anion sensor can be used with no problem.

The anion exchanger or the condensate with which a surface of the anion exchanger is coated generally functions as an elaborated membrane. The condensate is formed of an amine compound. In a dissociated basic material such as a quaternary ammonium salt, an amino group is easily caused to become protons or a cleaving reaction on a molecular chain is easily performed at a pH lower than pKa (acid dissociation coefficient). Under a condition that the internal solution (internal gel liquid) is in a range from being acidic to being alkaline, protons do not transition to the membrane, the amino group of the condensate with which the anion exchanger is coated is not caused to become protons, and the condensate accomplishes the function as the elaborated membrane. Thus, it is considered that the selectivity is maintained.

Comparative Example 1

As a comparative example, the pH buffer solution using NaCl and KCl as a base was added and had pH 1.0. The internal solution (internal gel liquid) was prepared so as to cause the concentration of chlorine ions in the internal solution (internal gel liquid) to be 90 mmol/L to 100 mmol/L. The storing time limit of the anion sensor manufactured by using the prepared internal solution was estimated.

The internal solution (internal gel liquid) having pH 1.0 was prepared by adding any of $H_3BO_3$, $CaCl_2$, and HCl to NaCl or KCl or by adding combination of $H_3BO_3$, $CaCl_2$, and HCl to NaCl or KCl. In addition, the internal solution (internal gel liquid) having pH 1.0 was prepared by adding any of the following buffer solutions to NaCl or KCl: a hydrochloric acid-potassium chloride buffer solution, a glycine-HCl buffer solution, a citrate buffer solution, an acetate buffer solution, a citrate-phosphate buffer solution, and a phosphate buffer solution. The anion sensor was filled with the prepared internal solution (internal gel liquid) and the $HCO_3$ selection coefficient was measured. Thus, the shelf life of the anion sensor was examined. The shelf life and a storing examination method of the anion sensor were similar to those in Example 1.

FIG. 5 illustrates the shelf life of the internal solution (internal gel liquid) having pH 1.0. A transverse axis indicates pH of the internal solution (internal gel liquid) and a longitudinal axis indicates the shelf life. When the internal solution (internal gel liquid) has pH 1.0, the $HCO_3$ selection coefficient exceeds 0.30 within one year.

The anion exchanger or the condensate with which a surface of the anion exchanger is coated generally functions as an elaborated membrane. The condensate is formed of an amine compound. In a dissociated basic material such as a quaternary ammonium salt, an amino group is easily caused to become protons or a cleaving reaction on a molecular chain is easily performed at a pH lower than pKa (acid dissociation coefficient). Under a condition that the internal solution (internal gel liquid) is acidic, protons gradually transition to the membrane, the amino group of the condensate with which the anion exchanger is coated is caused to become protons, and the condensate does not accomplish the function as the elaborated membrane due to showing of an ion-response function in the condensate. Thus, it is considered that deterioration is accelerated and the selectivity is degraded.

REFERENCE SIGNS LIST

1: sensor body,
2: chlorine ion-sensitive membrane,
3: flow channel,
4: internal electrode,
5: internal solution (internal gel liquid),
6: concave portion,
7: electrode terminal,
8: convex portion,
9: O-ring

The invention claimed is:
1. An anion sensor comprising:
an ion electrode membrane where an anion exchange membrane containing a cation compound is coated with a material containing an amine compound which has an ionization group of a predetermined pKa;
a container which defines a space which accommodates an internal solution, a flow channel configured to receive a sample therein disposed in the container, wherein the ion electrode membrane is disposed in the container with a portion or an entirety of a first surface of the ion electrode membrane in contact with the flow channel and a portion or an entirety of a second surface of the ion electrode membrane in contact with the internal solution; and
an electrode disposed in contact with the internal solution,
wherein the ion electrode membrane, the internal solution, and the electrode are disposed in the container,
wherein the internal solution contains NaCl or KCl and a pH buffer solution,
wherein the pH buffer solution is an ammonium chloride buffer solution,
wherein pH of the internal solution is adjusted so as to be equal to or greater than the pKa of the amine compound having the ionization group, and
wherein pH of the adjusted internal solution has a value of pH 11.
2. The anion sensor according to claim 1, wherein a concentration of anions in the internal solution is equal to or greater than 1 mmol/L.

* * * * *